(12) United States Patent
Ding

(10) Patent No.: US 7,763,271 B1
(45) Date of Patent: *Jul. 27, 2010

(54) POLYMERIC MICELLE-BASED LOCAL DELIVERY METHODS AND DEVICES

(75) Inventor: Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/891,353

(22) Filed: Aug. 10, 2007

Related U.S. Application Data

(60) Provisional application No. 60/837,382, filed on Aug. 11, 2006.

(51) Int. Cl.
*A61F 13/00* (2006.01)

(52) U.S. Cl. ........................................ 424/424; 424/422

(58) Field of Classification Search ........................ None
See application file for complete search history.

(56) References Cited

U.S. PATENT DOCUMENTS

| | | | |
|---|---|---|---|
| 4,331,697 A | 5/1982 | Kudo et al. | |
| 5,069,899 A | 12/1991 | Whitbourne | |
| 5,236,570 A | 8/1993 | Ma et al. | |
| 5,270,046 A | 12/1993 | Sakamoto et al. | |
| 5,453,171 A | 9/1995 | Ma et al. | |
| 5,741,881 A | 4/1998 | Patnaik | |
| 5,770,563 A | 6/1998 | Roberts et al. | |
| 5,855,618 A | 1/1999 | Patnaik et al. | |
| 6,320,017 B1 * | 11/2001 | Ansell ........................ | 528/310 |
| 6,589,943 B2 | 7/2003 | Byun et al. | |
| 6,630,580 B2 | 10/2003 | Tsang et al. | |
| 7,357,942 B2 * | 4/2008 | Burke et al. ................. | 424/423 |
| 2004/0018228 A1 * | 1/2004 | Fischell et al. .............. | 424/450 |
| 2004/0253185 A1 * | 12/2004 | Herweck et al. ........... | 424/10.2 |
| 2004/0258726 A1 * | 12/2004 | Stupp et al. ................. | 424/423 |
| 2006/0216342 A1 * | 9/2006 | Torchilin et al. ............ | 424/450 |

OTHER PUBLICATIONS

Torchilin "Polymeric Immunomicelles: Carriers of Choice for Targeted Delivery of Water-Insoluble Pharmaceuticals", Drug Delivery Technology, vol. 4, No. 2, 12 pgs (2004).

* cited by examiner

*Primary Examiner*—Ann Y Lam
(74) *Attorney, Agent, or Firm*—Squire Sanders & Dempsey, LLP

(57) ABSTRACT

Methods using PEG-PE micelles for the local delivery of substantially water insoluble drugs and bioactive agents are disclosed.

15 Claims, 2 Drawing Sheets

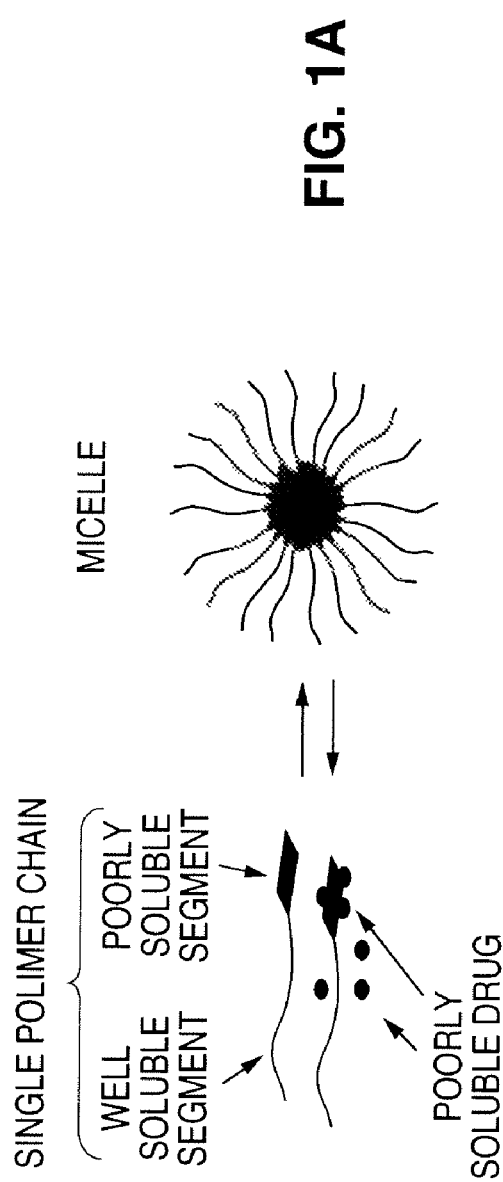
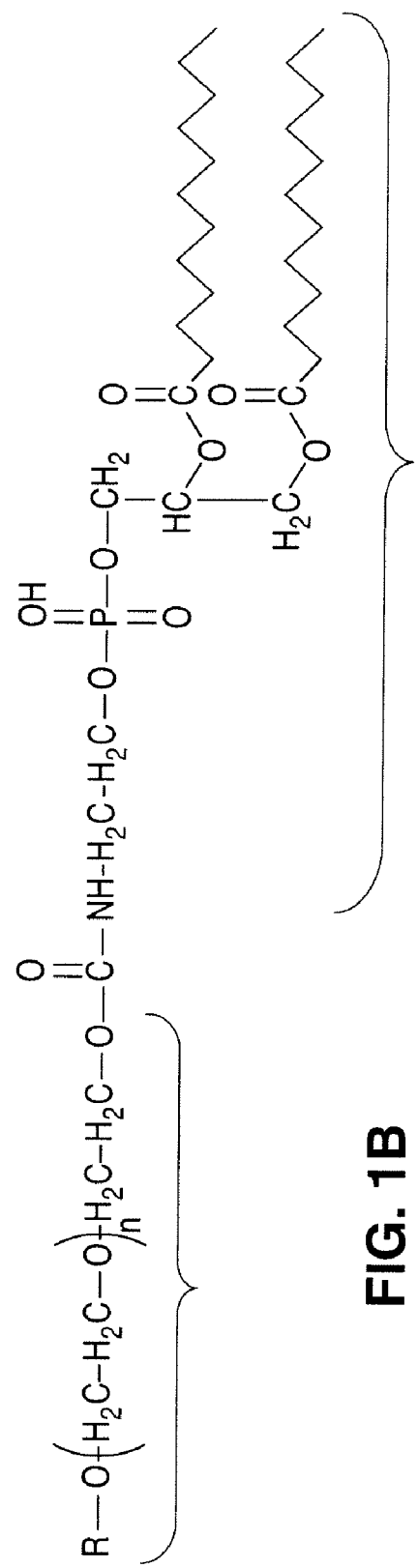
FIG. 1A
FIG. 1B

POLYMERIC MICELLE-BASED LOCAL DELIVERY METHODS AND DEVICES

PRIORITY

This document claims priority to Provisional Application Ser. No. 60/837,382, filed on Aug. 11, 2006.

FIELD

The present invention is directed to polymeric micelle-based local delivery methods for substantially water insoluble drugs and bioactive agents.

BACKGROUND

An ongoing goal of biomaterials research is to improve the materials from which medical articles, such as medical devices and coatings for medical devices, are produced. An example of such a medical article is an implantable medical device.

A stent is an example of an implantable medical device that can benefit from improvements such as biocompatible coatings that can be used as a vehicle for delivering pharmaceutically active agents in a predictable manner.

Stents play an important role in a variety of medical procedures such as, percutaneous transluminal coronary angioplasty (PTCA). Stents act mechanically to hold open or expand a passageway within a subject. But thrombosis and restenosis, conditions that may arise months after a particular procedure, are among the problems associated with the use of stents and can lead to additional angioplasty or a surgical by-pass operation.

To address these problems, stents are being developed to locally delivery agents, such as drugs or biologics. In some embodiments, local delivery includes coating the surface of a medical article, e.g., a stent, with a polymeric carrier and attaching an agent to or blending an agent with the polymeric carrier. These agents are useful alone or in combination with other agents. But a major disadvantage of this method is that the agents are released from the matrix through variable polymeric matrix morphology As a result, local agent delivery to tissues can be considered unpredictable.

The present invention is directed to overcoming these and other deficiencies in the art.

SUMMARY

Some embodiments of the present invention relate to a method for the local delivery of a substantially water insoluble drug. The method involves applying a polyamine primer layer to a stent, covalently attaching micelles, such as polyethylene-glycol-phosphatidyl-ethanolamine (PEG-PE) micelles, to the polyamine primer layer, loading a substantially water insoluble drug into the micelles, and implanting the stent. This method provides a means for the local delivery of a substantially water insoluble drug.

Micelles, such as polyethylene-glycol (PEG)-lipids, function to deliver water-insoluble drugs. One study employed PEG-PE micelles as a drug delivery carrier for the systemic deliver of poorly water-soluble drugs into a target lesion. It was found that polymeric micelle encapsulation increased the solubility, bioavailability, and half-life of poorly water-soluble drugs. Using micelles also improved the drug's pharmacokinetics and biodistribution. The present invention takes advantage of these properties and extends them to stent-based delivery of therapeutic agents. Several approaches encompassed by the present invention follow.

Some embodiments include the use of a polymeric micelle as a drug carrier to locally deliver a highly water-insoluble drug(s) via a stent. In this approach, the primer layer on the stent is a polyamine, e.g., polyethylene imine (PEI) or modified PEI, that possesses good adhesion properties with metal stents. PEG-PE is modified to contain amino reactive groups at the free terminal end of the PEG chain, such as p-nitrophenylcarbonyl (pNP), succinimidyl propionate (NHS), aldehyde, etc. (One of ordinary skill in the art will recognize that many micelle-forming materials can be similarly amino-reactive-group modified and can therefore form micelles suitable for use in the current invention.) After PEG-PE is covalently attached to a polyamine, i.e., PEI, water-insoluble and highly potent drugs such as sirolimus, everolimus, and paclitaxel can be loaded into the PEG-PE micelle. FIG. 1 is a schematic drawing of an immuno-micelle containing a poorly water-soluble drug.

This approach can provide for a thinner coating than current DES systems.

Alternatively, the reactive group on PEG-PE can be an amino group or a hydroxyl group so that PEG-PE can react with carboxyl groups on bioactive molecules and form covalent linkages. In addition, the thiol-reactive group can be the terminal functional group on the PEG, e.g., vinyl sulfone and thiols. The present invention also encompasses other PEG-lipids, such as PEG-distearoylphosphatidyl ethanolamine.

BRIEF DESCRIPTION OF THE DRAWINGS

FIGS. 1A-B are illustrations showing an immuno-micelle containing a drug and the structure of PEG-PE, respectively.

DETAILED DESCRIPTION

Figure 2:
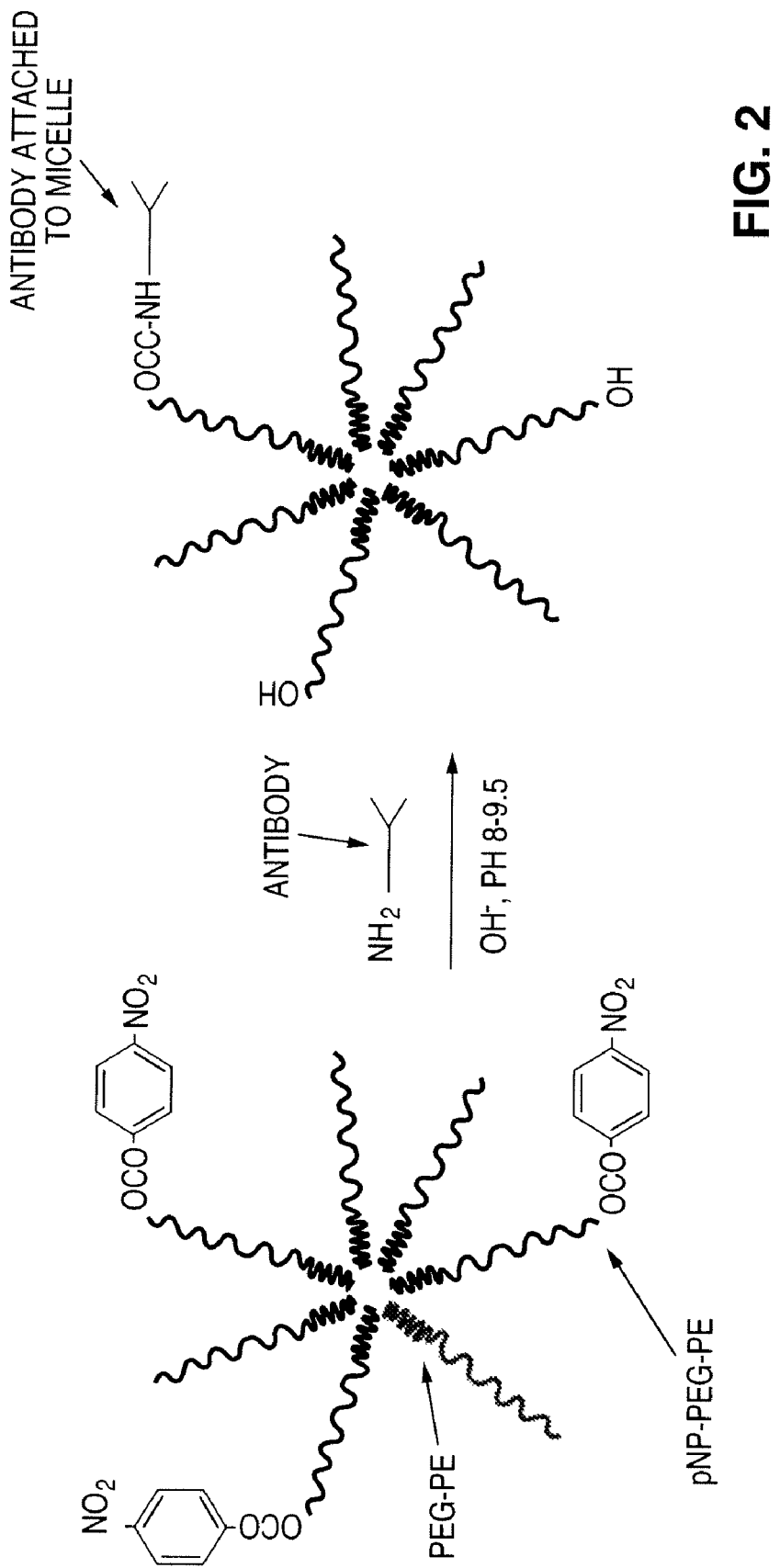
FIG. 2 is an illustration showing the covalent attachment of bioactive molecules to PEG-lipid.

Some embodiments of the present invention relate to a method for the local delivery of a substantially water insoluble drug. The method involves applying a polyamine primer layer to a stent, covalently attaching PEG-PE micelles to the polyamine primer layer, loading a substantially water insoluble drug into the PEG-PE micelles, and implanting the stent. This method provides a means for the local delivery of a substantially water insoluble drug. For purposes of this document, substantially water insoluble means having a solubility product less than that of a substance K. A substance K is a substance with a solubility product such that one of ordinary skill in the art would find the water solubility suitable for using the substance as a typical water soluble drug in mammalian vasculature. Alternatively, substantially water insoluble means having a solubility product of less than 0.5, 0.1, 0.05, 0.01, 0.005, 0.001, $5\times10^{-4}$, $1\times10^{-4}$, $5\times10^{-5}$, $1\times10^{-5}$, $5\times10^{-6}$, $1\times10^{-6}$, $5\times10^{-7}$, $1\times10^{-7}$, $5\times10^{-8}$, or $1\times10^{-8}$ times the solubility product of substance K.

Some embodiments of the present invention relate to a method for the local delivery of a bioactive molecule. The method involves covalently or otherwise attaching a bioactive molecule to micelles, such as PEG-PE micelles, to form a coating compound, applying the coating compound to a stent, and implanting the stent. This method provides a means for the local delivery of a bioactive molecule.

Some embodiments of the present invention relate to a method for the local delivery of a substantially water insoluble drug and a bioactive molecule. The method involves applying a polyamine primer layer to a stent, covalently attaching micelles, such as PEG-PE micelles, to the polyamine primer layer, loading a substantially water insoluble drug into the micelles, covalently attaching a bioactive molecule to the drug-loaded micelles, and implanting the stent. This method provides a means for locally delivering a substantially water insoluble drug and bioactive molecule.

Some embodiments of the present invention relate to a method for the local delivery of a substantially water insoluble drug and a bioactive molecule. The method involves coating the abluminal surface of a stent with substantially water insoluble drug-loaded micelles, such as PEG-PE micelles, coating the luminal surface of a stent with a bioactive molecule covalently or otherwise attached to micelles, and implanting the stent. This method provides a means for locally delivering a substantially water insoluble drug and bioactive molecule.

According to some embodiments of the present invention, substantially water insoluble drugs that can be locally delivered are known to those skilled in the art, but some specific examples are sirolimus, everolimus, zotarolimus, and paclitaxel analogs or derivatives that meet the definition of substantially water insoluble as defined above. Local delivery methods, i.e., the implantation of a stent, are also known to those skilled in the art.

According to some embodiments of the present invention, a stent is a medical device that can be implanted in a human or veterinary patient. Examples of stents include self-expandable stents and balloon-expandable stents. The underlying structure of the stent can be of virtually any design. The stent can be made of a metallic material or an alloy; the stent can be bioabsorbable; the stent can be polymeric in nature.

According to some invention embodiments, the primer layer includes a polyamine, such as polyethylene imine (PEI) or modified PEI.

According to some embodiments of the present invention bioactive molecules that can be locally delivered are known to those skilled in the art, but specific examples antibodies, proteins, super oxide dismutase (SOD) mimics, heparin and combinations thereof.

Micelles, e.g., polyethylene-glycol (PEG)-lipids, have been found to be able to deliver water-insoluble drugs. Specifically, one study showed that polyethylene-glycol phosphatidyl-ethanolamine (PEG-PE) could be used as a drug-delivery carrier for the systemic deliver of poorly water-soluble drugs into a target lesion. It was found that micelle encapsulation increased the solubility, bioavailability, and half-life of poorly water-soluble drugs. In addition, the use of the micelles also improved pharmacokinetics and biodistribution of the drug.

The present invention takes advantage of the unique properties of micelles and extends them to implant-based delivery of therapeutic agents.

In other embodiments, a polyamine primer layer, e.g., PEI, is applied to a medical device. PEG-PE, which is modified to contain amino reactive groups at the free terminal end of the PEG chain, is then covalently attached to the PEI primer layer. Next, water-insoluble and highly potent drugs, e.g., sirolimus, everolimus and paclitaxel, are loaded into the PEG-PE micellé. FIG. 1 is a schematic drawing of an immuno-micelle that contains a poorly water-soluble drug, in accordance with the present invention. This coated medical device can now be implanted into a patient for the local delivery of a water-insoluble drug.

In another embodiment, the micelle is used as an anchoring point for covalently attaching bioactive molecules. FIG. 2 is a schematic drawing of how PEG-PE micelle reacts with an antibody, e.g., an anti-CD34 antibody. Thus, a coating consisting of the polymeric micelle-bioactive molecules can then be attached to a polyamine primer on a stent or on the top of an existing drug eluting stent (DES) system. In the latter case, a polyamine is used as an adhesion layer between the DES and the PEG-PE micelle.

Another embodiment combines approaches 1 and 2. Specifically, a PEG-PE micelle coating that contains noncovalently attached drug(s), e.g., paclitaxel or everolimus, as described above according to approach 1, can be combined with covalently attached moieties, e.g., an antibody, protein, super oxide dismutase (SOD) mimic, heparin or other biological active agents and combinations thereof, as described above in accordance with approach 2. This combination can then be coated onto a stent for local delivery, thereby providing a means for the local delivery of both a water-insoluble drug and a bioactive agent.

In some embodiments, the micelle can be used with a hydrophobic or a hydrophilic polymer, or a mixture of both. As used in this document, the hydrophobic refers to an attribute of a material that defines the degree of water affinity of the molecules of the material. Hydrophobicity and hydrophilicity are relative terms. Generally, hydrophobicity and hydrophilicity of a polymer can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;

ΔE is the energy of vaporization, cal/mole; and

V is the molar volume, $cm^3$/mole.

Representative hydrophobic polymers include, but are not limited to, poly(ester amide), polystyrene-polyisobutylene-polystyrene block copolymer (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly(trimethylene carbonate), poly(ortho ester), polyphosphazenes, poly(phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly(vinylidene fluoride-co-hexafluoropropylene) (PVDF-HFP), poly(vinylidene fluoride-co-chlorotrifluoroethylene) (PVDF-CTFE), poly(methacrylates) such as poly(butyl methacrylate) (PBMA) or poly(methyl methacrylate) (PMMA), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(ureaurethanes) and a combination thereof. Methods of derivatizing heparin with hydrophobic materials or polymers are described in, for example, U.S. Pat. Nos. 4,331,697; 5,069,899; 5,236,570; 5,270,046; 5,453,171; 5,741,881; 5,770,563; 5,855,618; 6,589,943 and 6,630,580.

Representative hydrophilic polymers include, but are not limited to, polymers and co-polymers of PEG acrylate (PEGA), PEG methacrylate, 2-methacryloyloxyethyl phosphoryl choline (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, and 3-trimethylsilylpropyl methacrylate (TMSPMA), poly(ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), poly(L-lysine-ethylene glycol) (PLL-g-PEG), poly(L-g-lysine-hyaluronic acid) (PLL-g-HA), poly(L-lysine-g-phosphoryl choline) (PLL-g-PC), poly(L-lysine-g-vinylpyrrolidone) (PLL-g-PVP), poly(ethylimine-g-ethylene glycol) (PEI-g-PEG), poly(ethylimine-g-hyaluronic acid) (PEI-g-HA), poly (ethylimine-g-phosphoryl choline) (PEI-g-PC), and poly (ethylimine-g-vinylpyrrolidone) (PEI-g-PVP), PLL-co-HA, PLL-co-PC, PLL-co-PVP, PEI-co-PEG, PEI-co-HA, PEI-co-PC, and PEI-co-PVP, hydroxy functional poly(vinyl pyrrolidone), polyalkylene oxide, dextran, dextrin, sodium hyaluronate, hyaluronic acid, elastin, chitosan, acrylic sulfate, acrylic sulfonate, acrylic sulfamate, methacrylic sulfate, methacrylic sulfonate, methacrylic sulfamate and combination thereof. The non-fouling polymer can be, for example, poly(ethylene glycol), poly(alkylene oxide), hydroxyethyl-methacrylate (HEMA) polymer and copolymers, poly(n-propylmethacrylamide), sulfonated polystyrene, hyaluronic acid, poly(vinyl alcohol), poly(N-vinyl-2-pyrrolidone), sulfonated dextran, phosphoryl choline, choline, and combinations thereof.

Therapeutic Substances

For purposes of the current invention therapeutic substances or drugs can be divided into two categories: water soluble and substantially water insoluble. In some invention embodiments combinations of drugs are used including combinations of substantially water insoluble drugs and combinations of water soluble and substantially water insoluble drugs. In some embodiments, substantially water insoluble drugs include substantially water insoluble derivatives or analogs of otherwise water soluble drugs. Generally, throughout this disclosure, the term "drug" and "therapeutic substance" are used interchangeably. The therapeutic substance can be any agent which is biologically active.

The therapeutic substance can be, for example, a therapeutic, prophylactic, or diagnostic agent. As used herein, the therapeutic substance includes a bioactive moiety, derivative, or metabolite of the therapeutic substance.

Examples of suitable therapeutic and prophylactic agents include synthetic in-organic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Other examples of therapeutic substances include antibodies, receptor ligands, and enzymes, adhesion peptides, oligosaccharides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy, In some embodiments, the therapeutic substance can be for inhibiting the activity of vascular smooth muscle cells. More specifically, the therapeutic substance can be aimed at inhibiting abnormal or inappropriate migration or proliferation of smooth muscle cells for the inhibition of restenosis. The therapeutic substance can also include any substance capable of exerting a therapeutic or prophylactic effect in the practice of the present invention. For example, the therapeutic substance can be a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. The therapeutic substance can also fall under the genus of antineoplastic, cytostatic or anti-proliferative, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, recombinant hirudin, and thrombin inhibitors such as Angiomax ä (Biogen, Inc., Cambridge, Mass.). Examples of cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Other therapeutic substances include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, antibodies such as CD-34 antibody, abciximab (REOPRO), and progenitor cell capturing antibody, pro-healing therapeutic substances that promotes controlled proliferation of muscle cells with a normal and physiologically benign composition and synthesis products, enzymes, anti-inflammatory agents, antivirals, anticancer drugs, anticoagulant agents, free radical scavengers, estradiol, steroidal anti-inflammatory agents, non-steroidal anti-inflammatory, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy) ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, cytostatic agents, aspirin, and a combination thereof.

The foregoing substances are listed by way of example and are not meant to be limiting. Other active agents which are currently available or that may be developed in the future are equally applicable.

The dosage or concentration of the therapeutic substance required to produce a favorable therapeutic effect should be less than the level at which the therapeutic substance produces toxic effects and greater than the level at which nontherapeutic results are obtained. The dosage or concentration of the therapeutic substance can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device, Medical Device or Implantable Medical Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). Implantable medical devices include drug-eluting balloons. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Another embodiment includes using an abluminal coating employing the methods of approach 1 and a luminal coating employing the methods of approach 2. The coating method may be modified by using, for example, an abluminal coater, or electro-spray coater. The stent is then implanted in a patient allowing for the local delivery of a water-insoluble drug and a bioactive agent.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects (such as monomer type) composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists in which that aspect specifically excludes that aspect.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

The invention claimed is:

1. A method comprising:
   applying a primer layer to a medical device;
   attaching PEG-PE micelles to the primer layer;
   loading a substantially water insoluble drug into the micelles; and
   implanting the medical device,
   thereby providing a means for locally delivering the substantially water insoluble drug;
   wherein the substantially water insoluble drug is selected from the group consisting of sirolimus, everolimus, zotarolimus, and combinations thereof;
   wherein the primer comprises a polymer selected from the group consisting of poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), and poly(ethylimine-g-vinylpyrrolidone) (PEI-g-PVP), PEI-co-PEG, PEI-co-HA, PEI-co-PC, and PEI-co-PVP.

2. The method of claim 1 wherein the medical device is a stent.

3. The method of claim 2 wherein the stent is composed of a bioabsorbable polymer.

4. The method of claim 1 wherein the step of attaching comprises covalently attaching micelles to the primer layer.

5. The method of claim 1 wherein the substantially water insoluble drug further comprises paclitaxel.

6. A method comprising:
   applying a polyamine primer layer to a stent;
   covalently attaching PEG-PE micelles to the primer layer;
   loading a substantially water insoluble drug selected from the group consisting of sirolimus, everolimus, zotarolimus, and combinations thereof into the micelles; and
   implanting the stent;
   wherein the polyamine is selected from the group consisting of poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), and poly(ethylimine-g-vinylpyrrolidone) (PEI-g-PVP), PEI-co-PEG, PEI-co-HA, PEI-co-PC, PEI-co-PVP, and a combination thereof.

7. The method of claim 6 wherein the substantially water insoluble drug further comprising paclitaxel.

8. A device comprising:
   a base;
   a primer layer disposed over at least part of the base; and
   PEG-PE micelles attached to the primer layer, wherein the micelles contain a substantially water insoluble drug;
   wherein the substantially water insoluble drug is selected from the group consisting of sirolimus, everolimus, zotarolimus, and combinations thereof;
   wherein the primer comprises a polymer selected from the group consisting of poly(ethylimine-g-ethylene glycol) (PEI-g-PEG), poly(ethylimine-g-hyaluronic acid) (PEIg-HA), poly(ethylimine-g-phosphoryl choline) (PEI-g-PC), and poly(ethylimine-g-vinylpyrrolidone) (PEI-g-PVP), PEI-co-PEG, PEI-co-HA, PEI-co-PC, and PEI-co-PVP.

9. The device of claim 8 wherein the micelles are covalently attached to the primer layer.

10. The device of claim 8 wherein the substantially water insoluble drug further comprises paclitaxel.

11. A device comprising:
a base;
a polyamine primer layer disposed over at least part of the base; and
PEG-PE micelles covalently attached to the primer layer, wherein the micelles contain a substantially water insoluble drug;
wherein the substantially water insoluble drug is selected from the group consisting of sirolimus, everolimus, zotarolimus, and combinations thereof;
wherein the polyamine is selected from the group consisting of poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), and poly(ethylimine-g-vinylpyrrolidone) (PEI-g-PVP), PEI-co-PEG, PEI-co-HA, PEI-co-PC, PEI-co-PVP, and a combination thereof.

12. The device of claim 11 wherein the primer layer further comprises a hydrophobic polymer.

13. The device of claim 11 wherein the primer layer further comprises a hydrophilic polymer.

14. The device of claim 11 wherein the substantially water insoluble drug further comprises paclitaxel.

15. The device of claim 11 wherein the substantially water insoluble drug has a solubility product of less than $1 \times 10^{-3}$ times that of a water soluble drug.

* * * * *